United States Patent [19]

Rosenthal

[11] Patent Number: 4,692,620
[45] Date of Patent: Sep. 8, 1987

[54] NEAR INFRARED MEASURING INSTRUMENT WITH SAMPLE HOLDER

[75] Inventor: Robert D. Rosenthal, Gaithersburg, Md.

[73] Assignee: Trebor Industries, Inc., Gaithersburg, Md.

[21] Appl. No.: 739,679

[22] Filed: May 31, 1985

[51] Int. Cl.⁴ ..................... G01N 21/03; G01N 21/35
[52] U.S. Cl. .................................. 250/343; 250/339;
250/341; 356/246; 356/409; 356/440
[58] Field of Search ............... 356/246, 440, 436, 409,
356/414; 250/328, 339, 341, 359.1, 343

[56] References Cited

U.S. PATENT DOCUMENTS

| | | | |
|---|---|---|---|
| 3,194,111 | 7/1965 | Saunders | 250/343 |
| 3,521,964 | 7/1970 | Wilkes, Jr. | 250/343 |
| 3,523,737 | 8/1970 | Wood et al. | 356/409 |
| 3,526,462 | 9/1970 | McCurdy et al. | 356/246 |
| 3,646,313 | 2/1972 | Gorgone et al. | 356/246 |
| 4,030,837 | 6/1977 | Kojima et al. | 356/30 |

FOREIGN PATENT DOCUMENTS 1498816  3/1969  Fed. Rep. of Germany ...... 356/246

OTHER PUBLICATIONS

Holden et al, "A Variable Thickness Low Temperature Infra-Red Cell", J. Opt. Soc. Am., 40 (11), Nov. 1950, pp. 757–760.
Technicon Instruments Corp.-brochure, date unknown, "The Analytical Laboratory of the Future . . . Today!".
Pacific Scientific-brochure, "Model 101 Cereal Grain Analyzer", Feb. 1982.
Dickey-John Corporation-brochure, date unknown, "The Application-Matched Family of NIR Analyzers".

Primary Examiner—Carolyn E. Fields
Attorney, Agent, or Firm—Bernard, Rothwell & Brown

[57] ABSTRACT

Near infrared instrument for measuring constituents such as moisture, protein and oil in materials has a movable sample holder of predetermined thickness depending upon the particular material being measured. The sample holder is moved past a source of near infrared radiation and detector by a mechanical drive.

15 Claims, 7 Drawing Figures

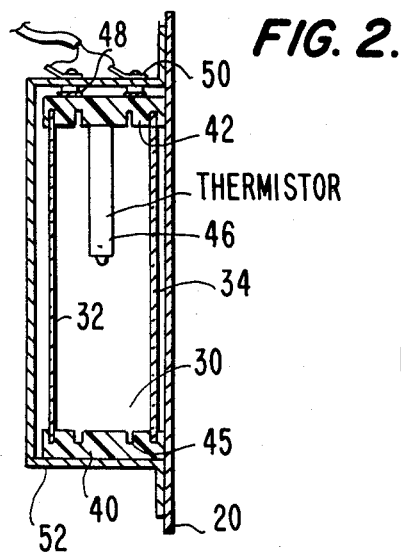

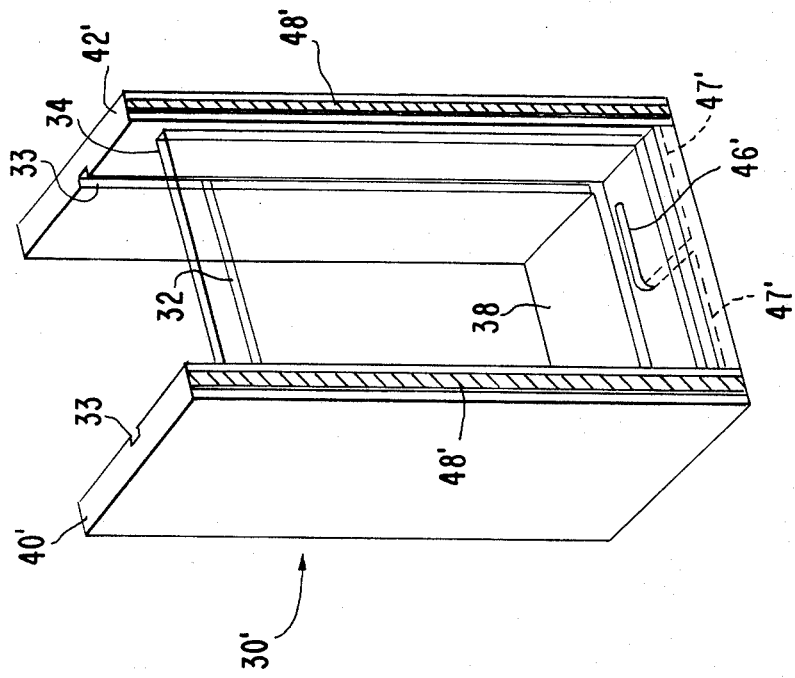
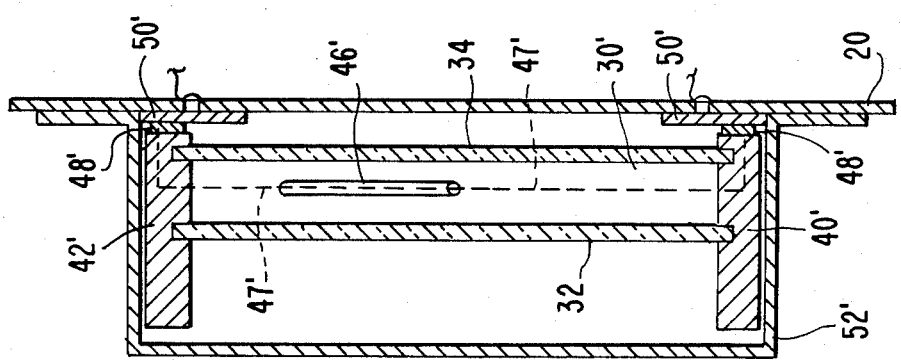

NEAR INFRARED MEASURING INSTRUMENT WITH SAMPLE HOLDER

BACKGROUND OF THE INVENTION

1. Field of the Invention

This invention relates to improvements in near infrared measuring instruments, and particularly such instruments that are utilized for measuring constituents, such as protein, moisture and oil in materials using near infrared radiation on a nondestructive basis.

2. Description of the Background Art

Near infrared measuring instruments that provide an accurate measure of constituents, such as protein, moisture and oil in grain and other products utilizing near infrared radiation are known in the art and have become commercially successful. Such instruments are particularly useful for measuring protein, oil and moisture in cereal grain in a totally nondestructive mode to a high degree of accuracy and with superior speed. Such instruments are commercially available from Trebor Industries, Inc. in Gaithersburg, Maryland, and are sold for example under the trademark TREBOR-90 and are disclosed in U.S. Pat. Nos. 4,286,327 and 4,404,642, inter alia.

These known instruments have proven to be commercially successful. Nevertheless, even though commercially successful they do have certain limitations. One of the most important of these limitations results from the fact that different types of grain and other materials have grossly different optical characteristics. For example, a fifteen millimeter cross-section of wheat has an optical density of between 4 and 5 (optical density is defined as the log (1/T) where T is the fraction of light transmitted through the sample). A fifteen millimeter cross-section of corn has much less optical density (i.e., it is much more transparent). Sunflower seeds have an optical density much greater than wheat and are practically optically opaque in an instrument with a fifteen millimeter cross-section. Rape seed are similar to sunflower seeds with regard to optical density.

To at least partially overcome the limitation due to the different optical densities of different grains, the TREBOR commercial instruments include in their instrumentation dual electronic gain to allow the same instrument to measure two different types of grain, for example, corn as well as wheat. However, the use of dual electronic gain does not work well on materials that are more optically opaque and therefore TREBOR manufactures separate instruments with a much smaller cross section thickness for sunflower seed and rape seed as well as for other cereal grains such as millet, etc. This need for separate instruments or different circuits in the same instrument for different types of grains hinders the usefulness, versatility and marketability of the instruments because most grain elevators handle a wide variety of grain and would prefer to utilize a single instrument for any grain they handle.

A further limitation with the existing commercial products is that the ejection wheel system for grain does not operate well on all types of grain. An ejection wheel works extremely well on wheat, barley, corn, soy bean and milo and on other grain products where the grain kernels are essentially solid in nature. However, it has been recently discovered that on long-grain rice, i.e., rice that has a very long "tail", the ejection wheel begins to jam. Although this is not a major limitation, it does cause concern and does limit the usefulness and versatility of the instrument.

Further, in the known prior art instruments, measurements of grain must be taken after the grain has stopped moving. The time it takes for the grain to stop moving varies with the wetness, temperature and random orientation of the grains. The prior art instruments have had to be adapted to accommodate the maximum time of grain movement and thus have built-in inefficiencies timewise. In other words, the ejection wheel which moves the grain must be able to move the grain independent of the moisture and temperature level of the grain, but the grain must stop moving in order to take an accurate measurement. As the ejection wheel gets older and wears or as damage occurs, such wheels need to be replaced causing undesirable "down time".

The limitations of the prior art ejection wheel type of instruments have also made them unsuitable for measuring constituents present in materials such as flours, meals, liquids, pastes and the like.

These problems and limitations with the known prior art have existed for the years since the Trebor instruments have been on the market with no overall satisfactory solution even though there has been an incentive to overcome such limitations.

SUMMARY OF THE INVENTION

The present invention eliminates moving of loose material past a stationary measuring station and eliminates utilizing an ejection wheel to discharge the material from a measuring column. In the present invention material to be measured is placed in a stationary cuvette or sample holder and the cuvette is moved bodily past a stationary measuring station. The same instrument can handle a large number of cuvettes having different cross-sectional thicknesses or a single cuvette could be adjusted for different cross-sectional thicknesses, thus a single instrument can measure any type of grain from sunflower seed and rape seed to corn, as well as such materials as meals, flours, liquids and pastes.

Because the material to be measured is stationary relative to the cuvette, no motion of the material relative to the cuvette can occur during measurement. The cuvette is moved by any suitable means of positive movement mechanism and it can be positively stopped prior to measurement.

The motion of the cuvette is not a function of the type of material to be measured and the instrument stays totally clean because no material is ever present in the mechanism portion of the instrument.

Moreover, since the material is contained within a cuvette, no material, dust, fluid or other residue of the material ever enters the instrument and this eliminates otherwise normal preventive maintenance requirements.

Additionally, use of a sealed cuvette provides an opportunity for permanent calibration samples. This eliminates having to have new calibration samples as in the prior art commercial instruments and contributes to a major cost saving in the production of such instruments.

BRIEF DESCRIPTION OF THE DRAWINGS

FIG. 1 is a partially schematic sectional elevational view of an infrared measuring instrument according to this invention.

FIG. 2 is a sectional view taken along line 2—2 of FIG. 1.

FIG. 3 is a front elevation view of a portion of the instrument shown in FIG. 1.

FIG. 4 is a perspective view of one embodiment of a sample holder for an instrument according to this invention.

FIG. 5 is a perspective view of an insert for a modified sample holder of this invention.

FIG. 6 is a perspective view of a second embodiment of a sample holder for an instrument according to this invention.

FIG. 7 is a sectional view similar to FIG. 2, but including a sample holder as shown in FIG. 6.

DETAILED DESCRIPTION OF THE PREFERRED EMBODIMENTS

A near infrared non-destructive measuring and testing instrument 10 has a source of near infrared radiation 12 which is directed through a sample S and onto a detector 14. The output of the detector is fed to a microprocessor 16 and the results in the form of percentage of a constituent such as moisture, protein, or oil are displayed on a display 18. What has been generally described above is known in the art, is commercially available from Trebor Industries, Inc. of Gaithersburg, Maryland sold under the trademark TREBOR 90 and is disclosed in prior patents assigned to Trebor including U.S. Pat. Nos. 4,286,327 and 4,404,642.

It is the means for handling the sample S in the environment of such instrument which constitutes the present invention. The instrument 10 includes an instrument stand 20 having infrared transparent windows 22 and 24 in alignment between the source of near infrared radiation 12 and the detector 14. Window 24 preferably includes an electrically conductive material, e.g., wire mesh, which is grounded to the instrument electronics to shield the detector 14 from electromagnetic interference in the environment. A motor 25 has a driven shaft 26 connected to a cam 28. This cam, in the nature of an eccentric, provides a step-by-step basis drive. The motor 25 is controlled from the microprocessor 16 and suitable means in the microprocessor may be used to control the synchronism of stopping of movement of the cam 28 and the taking of the measurements.

In one embodiment, a sample S of grain or other material is contained with a sample holder or cuvette 30. An entire cuvette according to this embodiment is shown in FIG. 4. The cuvette has near infrared radiation transparent sides 32 and 34, e.g., of glass, and near infrared opaque top and bottom 36 and 38 and sides 40 and 42 making a rectangular parallelopiped with two near infrared transparent sides and being hollow for containing a sample. The top 36 is removable and has grooves 44 for mating with the sides 32 and 34. Similar grooves 45 may be contained in the sides 40 and 42 and additional grooves may be positioned between the grooves shown in FIG. 2 so that the sides 32 and 34 may be moved closer together, thus diminishing the thickness of the space between the sides and hence the thickness of the sample and the sample holder as desired. Alternatively, different sample holders of different thicknesses can be used for different materials to be measured.

Within the sample holder is a means for measuring the temperature of the sample as is disclosed in U.S. Pat. No. 4,404,642. Specifically, there is provided a thermister 46 which is connected by electrical leads 47 soldered to two copper-coated adhesive strips 48 on the side 42 of the sample holder 30, as shown in FIG. 4. Two conductive portions of beryllium copper or other conductive spring-type material 50 are positioned as shown in FIG. 2 in the top of track 52 for cooperating with the strips 48, thus providing the electrical connection for measuring the temperature of the sample. The track 52 is generally channel-shaped and is secured to the base 20 as shown in FIG. 2. The front surface of the track 52 includes the window 22, see FIG. 3.

FIGS. 6 and 7 show another embodiment of this invention, wherein parts illustrated therein which are substantially the same as those in FIGS. 1–4 bear the same reference numerals. According to this embodiment, a sample S of grain or other material is contained with a sample holder or cuvette 30'. An entire cuvette according to this embodiment is shown in FIG. 6. The cuvette has near infrared radiation transparent sides 32 and 34, e.g., of glass, and near infrared opaque bottom 38 and sides 40' and 42' making a rectangular container with two near infrared transparent sides and being hollow for containing a sample. Transparent side 32 fits within grooves 33 of cuvette 30' and is slidably removable therefrom.

Within the sample holder 30' is thermister 46' for measuring the temperature of the sample. Thermister 46' is connected by electrical leads 47' soldered to two copper-coated adhesive strips 48' on the back edge portions of sides 40' and 42' of the sample holder 30'. Two copper-coated adhesive strips or other conductive material 50' are positioned as shown in FIG. 7 within track 52 along the inside portion of stationary support 20 for cooperating with the strips 48', thus providing the electrical connection for measuring the temperature of the sample. The track 52 is generally channel-shaped as described above and is secured to the base 20 as shown in FIG. 2. The front surface of the track 52 includes the window 22 as described above and shown in FIG. 3.

The operation of the instrument with particular emphasis on a sample holder 30 or 30' will now be described. There would either be a separate sample holder 30 or 30' for separate types of material specially dimensioned for the optical density of the material, or a single sample holder 30 can have its thickness changed in the direction of the measuring infrared radiation, for example by moving the walls 32 and 34 inwardly and putting them in grooves 45 in the sides, end and top of sample holder 30. It is preferable, however, to have separate sample holders for separate materials. The sample of material would be put in the sample holder and the sample holder would rest on the cam 28. The cam would preferably have an anti-friction material around its periphery and the sample holder 30 or 30' would rest on the periphery of the cam by virtue of gravity while also resting on stationary support 20 within track 52. The motor 25 drives the sample holder in steps and measurements are taken at various stationary positions of the sample holder during a rotation of the cam 28. After the measurements are taken the sample holder may be removed from the top of the instrument by simply holding onto it and removing it and a new sample holder with the same material or a different sample holder with a sample of another material may be inserted. It is also highly desirable to have calibration samples available to use in calibrating the instrument prior to or in connection with testing of samples of material.

Because the material does not itself move within the sample holder 30 or 30', a measurement can be taken immediately upon each stop of the cam 28. Moreover, since there is no need to eject the sample S through the instrument, the problem of ejection wheel wear and other problems associated with the ejection wheel are obviated. Additionally, the instrument stays totally clean without grain being present in the mechanism portion and the motion of the sample holder is not dependent on the type of grain as is the ejection-type mechanism of the prior art. Since the cuvette 30 or 30' is stopped and stationary prior to any measurement, the measurements can be made quicker, thus saving time during operation.

For cereal grains which are extremely optically dense such as sunflower seed or rape seed, a modification of the sample holder or cuvette may be utilized in which the side walls 32 and 34 are narrowed so as to define an area approximately one sunflower seed thick, for example, when measuring sunflower seeds. Positioned in the cuvette would be a lattice member 54 of the type shown in FIG. 5 having lattice openings 56 approximately the size of a sunflower seed. The lattice would be the same thickness between the walls 32 and 34 of the sample holder and each hole 56 in the lattice would contain one sunflower seed. In that case the walls 32 and 34 would be modified so as not to be completely transparent, but would be opaque and have pin-hole openings in the area near the center of the holes 56 so that the near infrared radiation would go through these pin-hole openings and through the sunflower seeds, for example, in the holes 56 to be then detected by the detector 14.

Although only a portion is shown in FIG. 1, the instrument also preferably includes an enclosure means 58 for sealing the inside of the instrument from ambient light.

The present invention allows the measurement of constituents such as moisture, protein or fat contained in a wide variety of grains as well as grain products such as meals and flours. The invention can also be used to measure liquids, powders or other granular materials, and pastes such as cream cheese wherein the sample is placed in a sealable plastic bag. The air is squeezed out of the bag, the bag is sealed and placed between transparent sides 32 and 34 where the bag is forced into the proper thickness thereby allowing direct measurement. Use of a plastic bag has a negligible effect on the measurement and eliminates the need for cleaning the sample holder.

What is claimed is:

1. A near infrared measuring instrument for measuring a constituent of a material, the instrument being of the type having a source of near infrared radiation, a detector for near infrared radiation, a means for holding a sample between the source and the detector, and means for data processing connected to the detector to read the detector and measure a constituent in a sample of the material by the amount of near infrared radiation transmitted through the sample, with the improvements comprising:

(a) means for providing a plurality of different predetermined uniform thicknesses of samples to be measured, comprising at least one cuvette for holding a sample between the source and the detector, the cuvette having opposing faces with at least a portion thereof being transparent to near infrared radiation, the cuvette providing at least one predetermined uniform thickness between the source and the detector in order to hold a predetermined uniform thickness of sample, (b) means for moving the cuvette relative to the near infrared radiation source and the detector and for stepwise placing a plurality of locations of the radiation-transparent portion of the cuvette and the at least one predetermined uniform thickness of sample into relative stationary alignment between the source and the detector, (c) means for reading the detector when the cuvette is stationary, and (d) means in the cuvette for measuring the temperature of the sample.

2. An instrument as in claim 1 wherein the cuvette includes a movable wall means for uniformly varying sample thickness in order to accommodate different samples.

3. An instrument as in claim 1 wherein the cuvette is mounted in a track for moving the cuvette relative to the near infrared radiation source and the detector.

4. An instrument as in claim 3 wherein the means for moving the cuvette includes a mechanical eccentric driven by a motor.

5. An instrument as in claim 4 further comprising means for sealing the cuvette and the inside of the instrument from ambient light.

6. An instrument as in claim 1 wherein the thickness between the walls of the cuvette is equal to one layer of a cereal grain sample.

7. An instrument as in claim 6 wherein the cuvette has means therein for positioning individual grains a single layer thick, and wherein the faces of the cuvette which allow transmission of near infrared radiation have small holes in them for the transmission of such radiation.

8. An instrument as in claim 3 wherein the means for moving the cuvette includes an intermittently moving electric motor connected to an eccentric, the eccentric contacting the cuvette.

9. An instrument as in claim 1 wherein the means for moving the cuvette includes a mechanical eccentric driven by a motor, and wherein the cuvette is mounted in a track for movement by gravity and the eccentric driven by the motor opposes the gravity.

10. An instrument as in claim 1 wherein the temperature sensing means in the cuvette is a thermister and the connections are through slidably connected conductors on the edges of the cuvette.

11. An instrument as defined in claim 1 wherein the cuvette is filled with a calibration sample and sealed.

12. An instrument as defined in claim 1 wherein the cuvette comprises means for holding a liquid sample.

13. An instrument as defined in claim 1 wherein the cuvette comprises means for holding a powder sample or other granular material sample.

14. An instrument as defined in claim 1 wherein the cuvette comprises means for holding a paste sample.

15. The instrument as defined in claim 1 wherein the means for providing a plurality of different thicknesses of samples is comprised of a plurality of cuvettes of different thicknesses.

* * * * *